(12) United States Patent
Zhao

(10) Patent No.: US 7,780,290 B2
(45) Date of Patent: Aug. 24, 2010

(54) TORIC INTRAOCULAR LENS WITH SPATIALLY-VARIANT ASTIGMATISM

(75) Inventor: Huawei Zhao, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 211 days.

(21) Appl. No.: 12/035,370

(22) Filed: Feb. 21, 2008

(65) Prior Publication Data

US 2009/0213326 A1 Aug. 27, 2009

(51) Int. Cl.
*G02C 7/02* (2006.01)
(52) U.S. Cl. ........................ 351/176; 351/159
(58) Field of Classification Search ................. 351/159, 351/176, 177
See application file for complete search history.

(56) References Cited

U.S. PATENT DOCUMENTS

| 4,778,462 A | * | 10/1988 | Grendahl | 623/6.27 |
| 4,795,462 A | * | 1/1989 | Grendahl | 623/6.28 |
| 4,798,608 A | * | 1/1989 | Grendahl | 623/6.28 |
| 4,798,609 A | * | 1/1989 | Grendahl | 623/6.29 |
| 4,932,970 A | * | 6/1990 | Portney | 623/6.25 |
| 5,066,301 A | * | 11/1991 | Wiley | 623/6.13 |
| 5,652,638 A | * | 7/1997 | Roffman et al. | 351/161 |
| 5,796,462 A | * | 8/1998 | Roffman et al. | 623/6.24 |
| 6,142,625 A | * | 11/2000 | Sawano et al. | 351/161 |
| 6,457,826 B1 | | 10/2002 | Lett | |
| 6,491,721 B2 | | 12/2002 | Freeman et al. | |
| 6,533,416 B1 | | 3/2003 | Fermigier et al. | |
| 6,808,262 B2 | | 10/2004 | Chapoy et al. | |
| 6,923,539 B2 | | 8/2005 | Simpson et al. | |
| 6,923,540 B2 | | 8/2005 | Ye et al. | |
| 6,986,578 B2 | | 1/2006 | Jones | |
| 2002/0118337 A1 | | 8/2002 | Perrott | |
| 2004/0150789 A1 | | 8/2004 | Jones | |

FOREIGN PATENT DOCUMENTS

| EP | 0949529 A2 | 10/1999 |
| WO | 93/03409 | 2/1993 |
| WO | 03/009053 A1 | 1/2003 |

* cited by examiner

*Primary Examiner*—Joseph Martinez
*Assistant Examiner*—James R Greece

(57) ABSTRACT

An intraocular lens for correcting or reducing the astigmatism of a cornea includes a pupil that is spatially divided into discrete zones, with each zone having a particular astigmatism magnitude and astigmatism orientation. In one embodiment, the zones all have the same astigmatism magnitude, which is equal and opposite the cornea astigmatism magnitude to within a particular tolerance, such as 0.25 diopters. In one embodiment, some or all of the zones all have different astigmatism orientations, with the angular separation between astigmatism orientations being on the order of the rotational misalignment tolerance of the lens to the cornea. The visual performance of such a lens deteriorates more slowly with rotational misalignment, when compared to a comparable lens having a uniform astigmatism orientation across its entire pupil, leading to more relaxed tolerances for a surgeon that implants the lens.

12 Claims, 5 Drawing Sheets

Amounts: vary

Orientations: vary

Amounts: same

Orientations:
$\theta - \Delta/2$
$\theta + \Delta/2$

Amounts: same

Orientations:
θ
θ + Δ/2
θ − Δ/2

Amounts: same

Orientations:
θ − Δ/2
θ + Δ/2
θ − Δ/2
θ + Δ/2

Amounts: vary

Orientations:
θ − Δ/2
θ + Δ/2
θ − Δ/2
θ + Δ/2

Amounts: vary

Orientations:
vary

TORIC INTRAOCULAR LENS WITH SPATIALLY-VARIANT ASTIGMATISM

BACKGROUND OF THE INVENTION

1. Field of the Invention

This invention relates generally to an intraocular lens, and more specifically to an intraocular lens having at least two zones in which the astigmatism amount and/or orientation varies from zone-to-zone.

2. Description of the Related Art

There are many medical conditions that degrade the vision of a patient's eye. For instance, cataracts can cause the natural lens of an eye to become opaque. Fortunately, in many of these cases, the natural lens of the eye may be removed surgically and replaced with an intraocular lens, thereby restoring the vision of the eye.

Typically, the power required of the intraocular lens is determined by the properties of the patient's eye, which can include one or more refractive indices, curvatures, and/or distances. Any or all of these properties may be measured for a particular patient, so that a selected power for the intraocular lens matches the power required for a particular eye to within a particular tolerance, such as 0.25 diopters or 0.5 diopters.

In some cases, a particular cornea may have a rotational asymmetry that imparts astigmatism onto light that is transmitted through it. The astigmatism degrades the vision of the eye, and cannot be corrected by adjusting the power of the lens. In these cases, the intraocular lens may provide additional correction if it has a similar but opposite amount of astigmatism. Then, the astigmatism of the lens may cancel or reduce the astigmatism of the cornea, and the light reaching the retina of the eye may have reduced astigmatism and, therefore, may have improved vision.

In practice, there are difficulties with an equal-but-opposite astigmatism correction. In particular, there may be some residual astigmatism left in the eye, caused by a rotational misalignment between the astigmatic axis of the cornea and the astigmatic axis of the corrective intraocular lens. This rotational misalignment and its effects are shown in greater detail in the text that follows, and in FIGS. 1 and 2.

FIG. 1 is a schematic drawing of a lens pupil in the presence of astigmatism. (Strictly speaking, this is astigmatism balanced by defocus so that RMS wavefront error is minimized. In terms of wavefront error, FIG. 1 has a given amount of astigmatism $W_{22}$ with an additional amount of defocus $W_{20}$ given by $W_{20}=-W_{22}/2$. In terms of Zernike polynomials, FIG. 1 has a given amount of astigmatism corresponding to the fifth and/or sixth Zernike polynomial terms, depending on the orientation of the astigmatism; in FIG. 1 the fourth Zernike term, corresponding to defocus, is zero.)

The wavefront contour map 1 (labeled as "1") shows contours of equal phase in the pupil. In one direction, in this case the direction denoted by angle θ, the wavefront shows a negative curvature. In a direction perpendicular to that denoted by θ, the wavefront shows a positive curvature. At +/−45° degrees to θ, the wavefront is essentially flat.

For this document, the wavefront contour map 1 may be represented more simply by two equivalent schematic representations 2 and 3 (labeled as "2" and "3", respectively). Element 2 shows the pupil having a particular amount of astigmatism, denoted by +A, with an orientation denoted by θ. Note that the parallel lines in element 2 act as a guide for the viewer that show the orientation angle of the astigmatism, are not contours of equal phase. The "+" signs show regions of increasing phase in the pupil. Another representation, substantially equivalent to element 2, is element 3, in which an equal but opposite amount of astigmatism, denoted by −A, is oriented at 90° to that in element 2.

Using the drawing conventions of FIG. 1, FIG. 2 shows the effects of a rotational misalignment of a known lens that corrects for the astigmatism of a particular cornea.

The circles in FIG. 2 represent the pupil area of the eye. The pupils are shown for simplicity as being circular, but they may include elongations or deformations. In general, the pupil areas correspond to physical locations on the anterior and/or posterior surfaces of the intraocular lens, so that the center of the pupil corresponds to the center of the lens surfaces, the edge of the pupil corresponds to the edge of the lens surfaces, and so forth.

The leftmost circle represents the astigmatism of the cornea of a particular patient's eye. The cornea astigmatism may have any particular orientation in the eye, and may deviate significantly from horizontal or vertical. In FIG. 1, the orientation of the cornea astigmatism is represented by an angle θ.

In practice, the magnitude of astigmatism is typically reported in power, usually in diopters. Alternatively, astigmatism may be reported as an axial separation between two foci, although this is seldom done for the optics of the eye. As a further alternative, astigmatism may be reported in terms of wavefront error. The power error, the axial separation and the wavefront error may all be related simply to each other, and all are substantially equivalent for the purposes of this discussion. In FIG. 2, the magnitude of the cornea astigmatism is denoted by an amount −A.

The cornea, therefore, has an astigmatism that can be represented by its magnitude ("−A") and its orientation ("θ").

A known intraocular lens is shown schematically in the middle circle of FIG. 2. The lens itself has an equal and opposite amount of astigmatism as the cornea, which is denoted by the value +A. If this lens were to be implanted in the eye with its astigmatism precisely oriented to that of the cornea, then the corneal astigmatism would be completely or nearly completely cancelled. However, there is usually a small angular error in the orientation that arises during the implantation surgery, which is denoted in FIG. 2 as δ, so that the astigmatism of the lens is oriented at angle θ+δ after implantation. This angular error may be kept as small as possible, but may be limited in practice by the skill of the surgeon. While more skilled surgeons may be able to achieve a δ of about 5 degrees, less skilled surgeons may have difficulty meeting this value and may implant lenses with larger angular errors than 5 degrees.

Mathematically, it is found that the astigmatism of the cornea (amount −A, orientation θ), plus the astigmatism of the rotationally misaligned lens (amount +A, orientation θ+δ), results in a residual astigmatism with magnitude 2A sin δ, oriented at 45° to the angle (θ+δ/2).

It is instructive to provide a numerical example of this 2A sin δ quantity, to illustrate the magnitudes of residual astigmatism that may result from angular misalignment of the lens.

Consider a cornea that has 2 diopters of astigmatism, and a lens that has 2 diopters (of the opposite sign) of astigmatism. If the lens is implanted with an angular error δ of 5 degrees, which is a rather tight tolerance for a surgeon, then the residual astigmatism is (2) (2 diopters) (sin 5°) 0.35 diopters. For a looser tolerance of 10 degrees, the residual astigmatism is (2) (2 diopters) (sin 10°)=0.7 diopters.

A typical threshold for astigmatism is 0.25 diopters, so that if the light reaching the retina has less than 0.25 diopters of astigmatism, then the astigmatism does not significantly degrade the vision of the eye.

As a result, the residual astigmatism in the eye may impose a prohibitively tight tolerance on the angular orientation of the lens during implantation, resulting in a tedious and expensive implantation procedure.

Accordingly, there exists a need for an intraocular lens having a reduced angular orientation tolerance.

SUMMARY OF THE INVENTION

An embodiment is a multi-zonal ophthalmic lens having a pupil, the pupil comprising: a first zone having a first astigmatism, the first astigmatism having a first astigmatism magnitude and a first astigmatism orientation; and a second zone surrounding the first zone and having a second astigmatism, the second astigmatism having a second astigmatism magnitude and a second astigmatism orientation different from the first astigmatism orientation.

A further embodiment is a method of improving the vision of an eye having a cornea, the cornea having a cornea astigmatism, the cornea astigmatism having a cornea astigmatism amount and a cornea astigmatism orientation, with a lens, the method comprising: dividing a pupil of the lens into a plurality of discrete pupil segments; and providing an astigmatism to each of the plurality of discrete pupil segments, each astigmatism having an astigmatism amount and an astigmatism orientation. The astigmatism amounts of at least two pupil segments are equal to a lens astigmatism amount. The astigmatism orientations of the at least two pupil segments are different from each other.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following 14 figures, with like numerals indicating like parts.

DETAILED DESCRIPTION OF THE DRAWINGS

Figure 3:
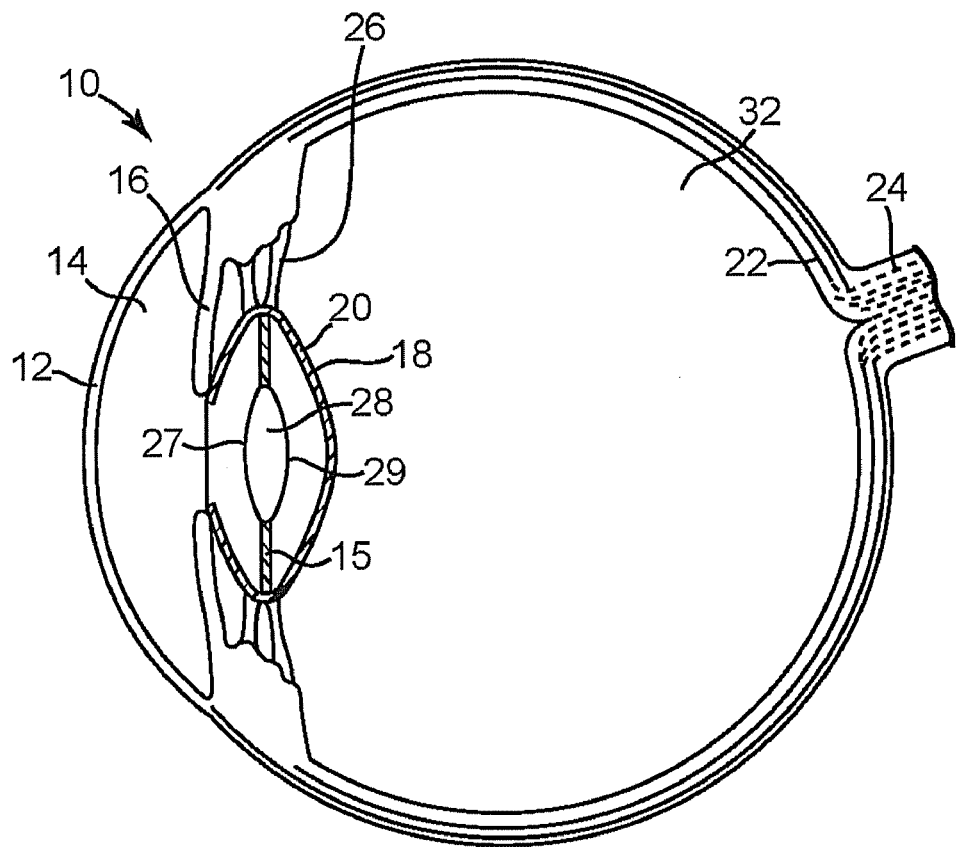
FIG. 3 is a schematic drawing of a human eye with an implanted intraocular lens.

FIG. 3 is a schematic drawing of a human eye 10, in which the natural lens of the eye has been removed and replaced with an intraocular lens. Light enters from the left of FIG. 1, and passes through the cornea 12, the anterior chamber 14, the iris 16, and enters the capsular bag 18. Prior to surgery, the natural lens occupies essentially the entire interior of the capsular bag 18. After surgery, the capsular bag 18 houses the intraocular lens, in addition to a fluid that occupies the remaining volume and equalizes the pressure in the eye. The intraocular lens is described in more detail below. After passing through the intraocular lens, light exits the posterior wall 20 of the capsular bag 18, passes through the posterior chamber 32, and strikes the retina 22, which detects the light and converts it to a signal transmitted through the optic nerve 24 to the brain.

The intraocular lens comprises an optic 28 and may include one or more haptics 15 that are attached to the optic 28 and may serve to center the optic 28 in the eye and/or couple the optic 28 to the capsular bag 18 and/or zonular fibers 26 of the eye.

The optic 28 has an anterior surface 27 and a posterior surface 29, each having a particular shape that contributes to the refractive properties of the lens. Either or both of these lens surfaces may optionally have a diffractive element made integral with or attached to the surfaces. The refractive and/or diffractive elements on the anterior and/or posterior surfaces may have anamorphic or toric features that can generate astigmatism. Typically, this astigmatism may be used to offset the astigmatism from a particular cornea in an eye.

The cornea astigmatism magnitude and orientation may be measured by surface profilometry or by reflected or transmitted wavefront measurements (e.g., using a Hartmann-Shack wavefront sensor, or the like). Once the astigmatism magnitude is determined, a lens may be selected or fabricated to reduce or at least partially cancel the corneal astigmatism. For example, a practitioner may select an intraocular lens from a kit of lenses, with each lens in the kit having a discrete value of astigmatism. The astigmatism values in the kit may be in increments of 0.25 diopters, 0.125 diopters, or any suitable value. Alternatively, the intraocular lens may be custom-designed and fabricated to offset the cornea astigmatism of a particular patient.

The intraocular lens has a pupil. For the purposes of the present disclosure, the pupil of an intraocular lens means the opening of a lens or optic that restricts the extent of a bundle of light rays from a distant source that can imaged or focused by the lens or optic. The lens pupil is usually circular and is specified by its diameter. Thus, the lens pupil represents the full extent of the lens or optic usable for forming the conjugate image of an object or for focusing light from a distant point source to a single focus or to a plurality of predetermined foci, in the case of a multifocal optic or lens. In some embodiments, the lens pupil has the same or substantially the same diameter as the optic. Alternatively, the diameter of the lens pupil may be smaller than the diameter of the optic, for example, due to the presence of a glare or PCO reducing structure disposed about a peripheral region of the optic. Many of the figures in this document show an exemplary pupil, when viewed from a position along the optical axis of the lens.

Figure 4:
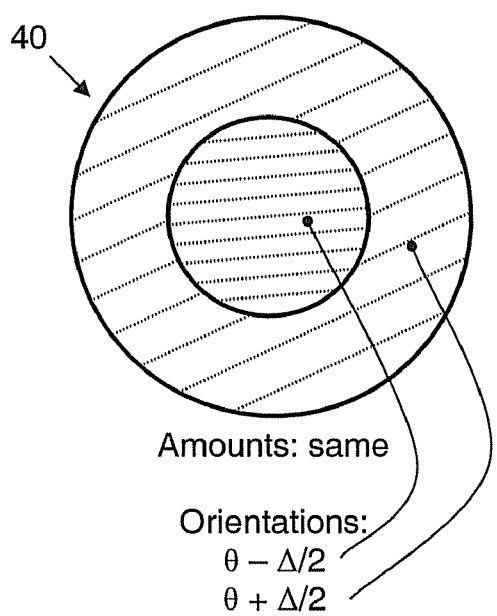
FIG. 4 is a schematic drawing of a pupil of an intraocular lens with two concentric zones, each zone having a different astigmatism orientation.

FIG. 4 is a schematic drawing of the pupil 40 of an embodiment of an intraocular lens. The pupil 40 is segmented into two concentric, radial zones. Each zone may include the same amount of astigmatism (denoted as amount "A") but with orientations that differ by an angle Δ. For example, if a nominal or average orientation of the astigmatism in the all the zones is at an angle θ, the orientations of the astigmatisms of the zones may be at "θ−Δ/2" and "θ+Δ/2".

The amount of astigmatism in each zone may be matched to the astigmatism of the cornea of the eye in which the lens is to be implanted. For instance, if the cornea has −2 diopters of astigmatism, then lens 30 may have +2 diopters of astigmatism in each zone. Alternatively, the zones may have powers that differ from that of the cornea and/or that differ from one another. In some embodiments, the lens 30 is part of a catalog or kit that includes lenses having discrete values of astigmatism, where a surgeon or practitioner chooses the amount of lens astigmatism that is closest to the equal and opposite value of the cornea astigmatism.

The astigmatisms in the two zones have orientations that differ by angle Δ. When the lens is perfectly aligned with a cornea astigmatism having orientation θ, the two zones have astigmatism orientations of θ−Δ/2 and θ+Δ/2. In practice, there may be a particular tolerance on the angular error of the lens that occurs during implantation, such as +/−5°, +/−10°, and so forth, with smaller tolerance numbers being harder for a surgeon to achieve. The angular separation of the orientations Δ may be related to the implantation angular tolerance δ, and may take on values of δ/4, δ/3, δ/2, δ, 2δ, 3δ, 4δ, and so forth. For instance, if the lens is specified to be implanted to within +/−5°, then the angular separation of the astigmatism orientations A may be 2.5°, 5° or 10°.

Figure 2:
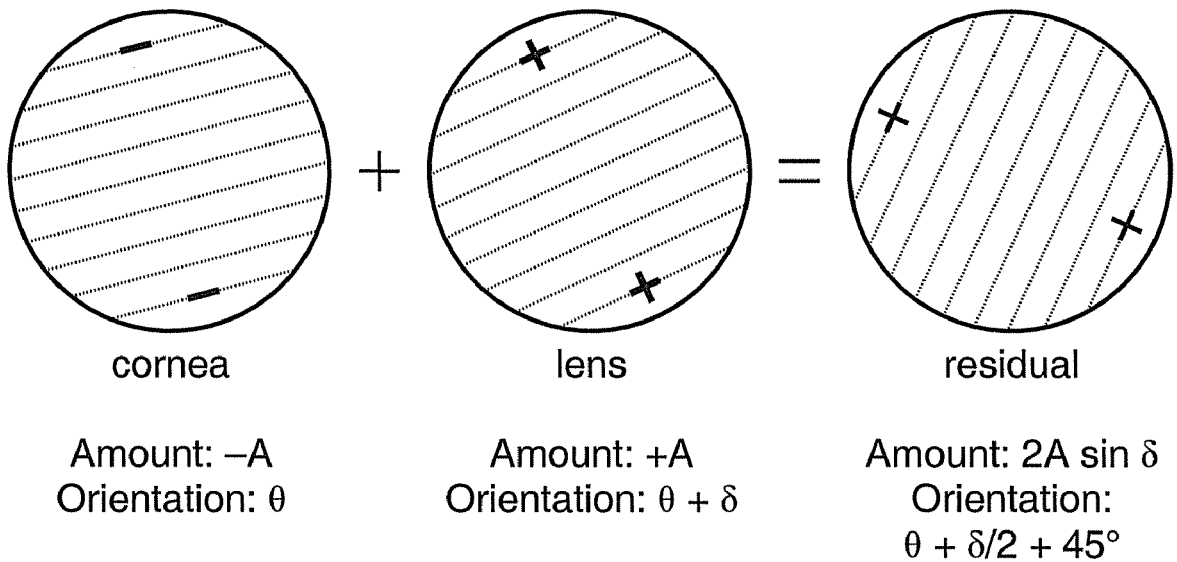
FIG. 2 is a schematic drawing of the residual astigmatism resulting from an astigmatic cornea and a known, rotationally misaligned, astigmatic lens.
Figure 5:
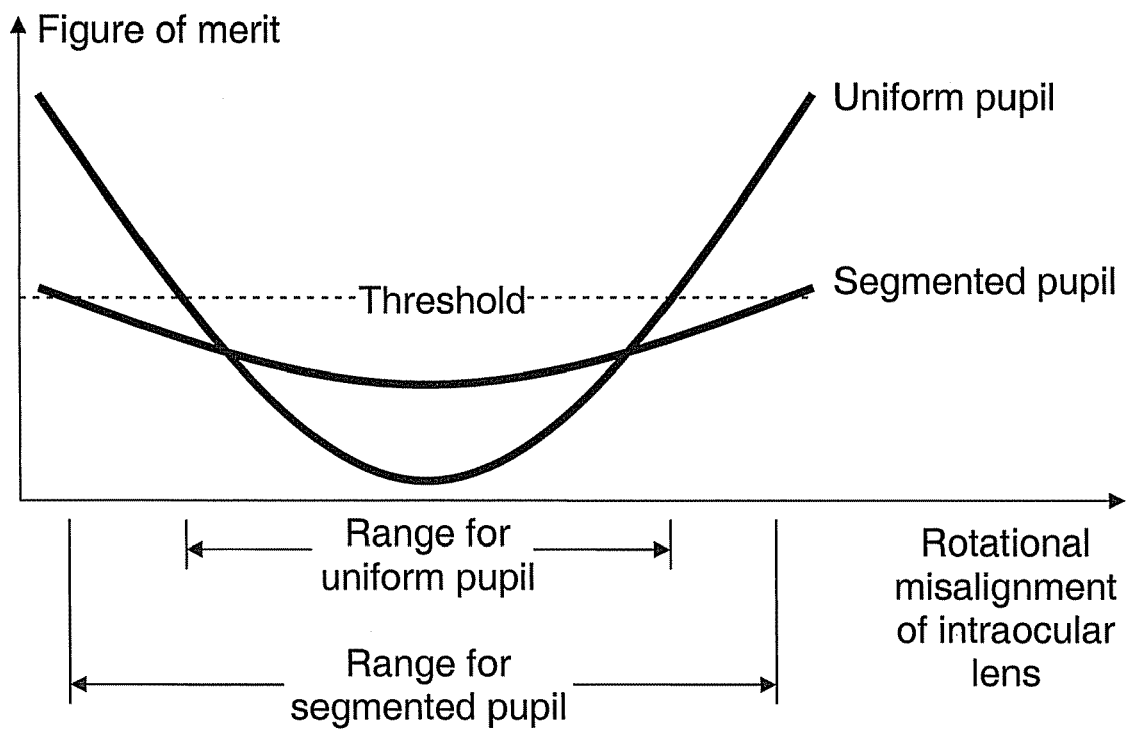
FIG. 5 is an exemplary plot of the relative performance of the lenses of FIGS. 2 and 4, as a function of rotational misalignment.

The benefits of such a segmented pupil may be seen in the plots of FIG. 5, which is a plot of performance versus rotational misalignment, for lenses having uniform pupils, such as the known lens of FIG. 2, and having segmented pupils, such as the lens of FIG. 4.

In FIG. 5, the horizontal axis is rotational misalignment, with minima for both curves occurring where the astigmatism of the intraocular lens is rotationally matched to the astigmatism of the cornea. The uniform pupil may have a better "optimal" value than the segmented pupil, but the slope away from this "optimal" value is generally larger for the uniform pupil. The figure of merit value may increase more slowly for the segmented pupil than for the uniform pupil, and may cross a particular threshold value at a larger rotational misalignment value than the uniform pupil. As a result, the segmented pupil may have a larger (or more loose) tolerance on rotational misalignment, which can ease the cost and/or difficulty of implantation.

The vertical axis is figure of merit which may be any suitable figure of merit used in vision or optics measurements. For instance, figures of merit that increase away from an optimal (minimum) value include RMS spot size, RMS wavefront error, Zernike polynomial values, wavefront error terms, point spread function dimension(s), or any other suitable figure of merit. Other figures of merit may decrease away from an optimal (maximum) value, which is the opposite of the exemplary plot of FIG. 5. One such figure of merit is linear Modulation Transfer Function (MTF) along a particular direction, at a particular spatial frequency, such as 25, 50, or 100 lines pairs per mm. Another figure of merit is rotational MTF at a particular rotational frequency, such as 30 circles per degree. Another figure of merit that decreases from an optimal maximum value may include Strehl Ratio.

Because the overall shape of the lens pupil in FIG. 4 is rotationally symmetric, it is possible to calculate analytically an RMS wavefront error that arises from rotational misalignment of an intraocular lens having such a pupil. The following paragraphs provide a non-limiting example of such a calculation.

Beginning with an expression for the wavefront aberration W as a function of normalized pupil coordinates ρ and θ, keeping only the terms corresponding to defocus and astigmatism oriented in direction $θ_0$:

$$W(\rho,\theta) = W_{20}\rho^2 + W_{22}\rho^2 \cos^2(\theta - \theta_0)$$

Figure 1:
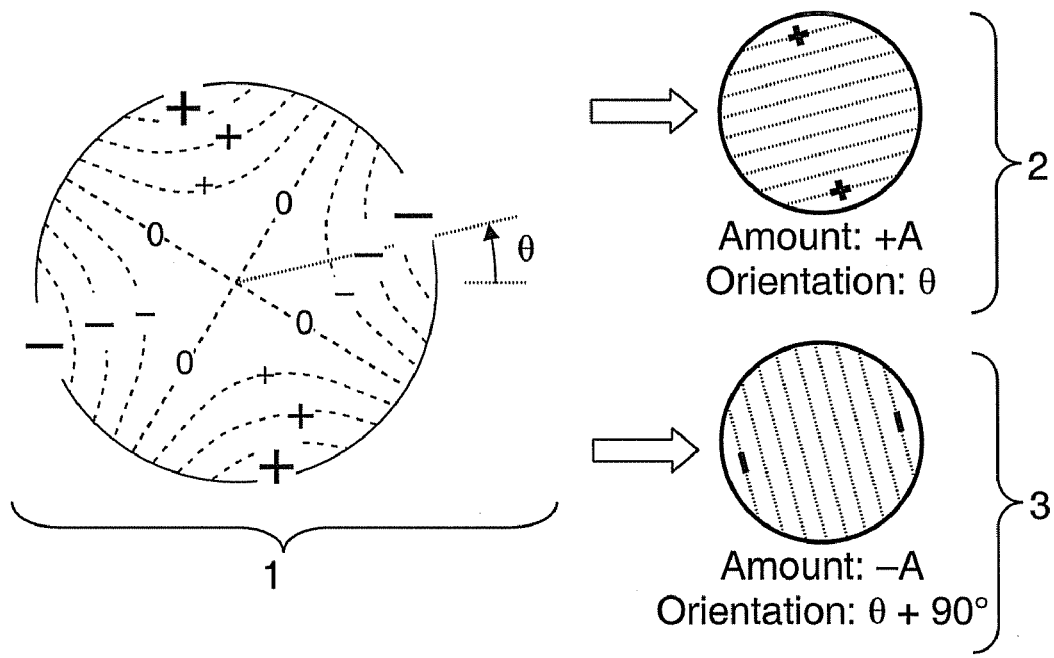
FIG. 1 is a schematic drawing of a lens pupil in the presence of astigmatism.

Assume that that the value of defocus $W_{20}$ is $-W_{22}/2$, so that the pupil wavefront appears as shown in FIG. 1. Rewrite the wavefront W as:

$$W(\rho, \theta) = W_{22}\rho^2 \frac{\cos[2(\theta - \theta_0)]}{2}$$

Calculate the wavefront variance, $\sigma_W^2$ for the wavefront $W(\rho, \theta)$ above:

$$\sigma_W^2 \equiv \langle W^2 \rangle - \langle W \rangle$$

$$= \frac{1}{\pi}\int_0^{2\pi}\int_0^1 W^2 \rho d\rho d\theta - \frac{1}{\pi}\int_0^{2\pi}\int_0^1 W\rho d\rho d\theta$$

$$= \frac{1}{4}\int_0^1 W_{22}^2 \rho^5 d\rho$$

The RMS wavefront error is the square root of the wavefront variance, given above.

Assume that the astigmatism $W_{22}$ is constant within each zone and is equal to $2A \sin(\delta - \delta_i)$ within each zone i. Each zone has astigmatism oriented at $\delta_i$ and is bounded by outer radius $\rho_i$ and inner radius $\rho_{i-1}$, and δ is the rotational misalignment of the intraocular lens. The wavefront variance becomes:

$$\sigma_W^2 = \frac{A^2}{24}\begin{bmatrix}(2 - 2\cos[2(\delta - \delta_1)])(\rho_1^6 - 0^6) + \\ (2 - 2\cos[2(\delta - \delta_2)])(\rho_2^6 - \rho_1^6) + \ldots + \\ (2 - 2\cos[2(\delta - \delta_i)])(\rho_i^6 - \rho_{i-1}^6) + \ldots + \\ (2 - 2\cos[2(\delta - \delta_n)])(1^6 - \rho_{n-1}^6)\end{bmatrix}$$

Consider the special case of two concentric zones. A first zone extends from the center of the pupil at ρ=0 to a radius of ρ=$ρ_0$, with an astigmatism of magnitude A and orientation +Δ/2. A second zone extends from the radius of ρ=$ρ_0$ to the edge of the pupil at ρ=1, with an astigmatism of magnitude A and orientation −Δ/2. The wavefront variance, $\sigma_W^2$, simplifies to $$\sigma_W^2 = \frac{A^2}{24}[2 - 2(\cos2\delta\cos\Delta - [1 - 2\rho_0^6]\sin2\delta\sin\Delta)]$$

As a check, this reduces to a single zone if $\rho_0=0$ or 1, with the expected result of $$\sigma_W^2 = \frac{A^2}{24}\left[4\sin^2\left(\sigma \pm \frac{\Delta}{2}\right)\right]$$

The preceding calculation applies when RMS wavefront error is used as the specific figure of merit. Other figures of merit may be used as well, including any or all of those listed above, although the algebra for these other figures of merit may be more cumbersome than for RMS wavefront error.

An advantage of the segmentation scheme of FIG. 4, in which the lens pupil is segmented into concentric portions, with each portion having the same amount of astigmatism but different orientations for each astigmatism axis, is that the resulting lens becomes less sensitive to rotational misalignment, during and/or after implantation. The peak performance of the segmented lens may be less than that of the uniform lens when each lens is optimally aligned; however, the performance of the segmented lens, as a function of rotational misalignment, may deteriorate more slowly than for the uniform lens. For example, as the performance of one segment decreases with rotational misalignment, the performance of the other may increase, wherein the performance of one segment partially offsets the other, thus decreasing sensitivity to rotational misalignment.

In FIG. 4, the pupil 40 is divided so that the central zone has a radius equal to roughly half the pupil radius, and an angular separation between astigmatism axes of $\Delta$. When optimally aligned to a cornea with astigmatism $\theta$, the two zones have astigmatism orientations of $\theta+/-\Delta/2$. The alignment tolerance $\delta$ on the lens may be on the order of $\Delta$, with $\delta$ being equal to $\Delta$ or being equal to $\Delta/4$, $\Delta/3$, $\Delta/2$, $2\Delta$, $3\Delta$, $4\Delta$, or any suitable multiplicative factor times $\Delta$. In other embodiments, the pupil 40 is divided so that the central zone has an area that is equal to roughly half the pupil area. Other radius or area ratios between the zones are anticipated in accordance with the particular requirements of a situation or design.

In addition to the geometry of FIG. 4, there are other possible geometries, shown in FIGS. 6-14, and described in a non-limiting way in the text that follows.

Figure 6:
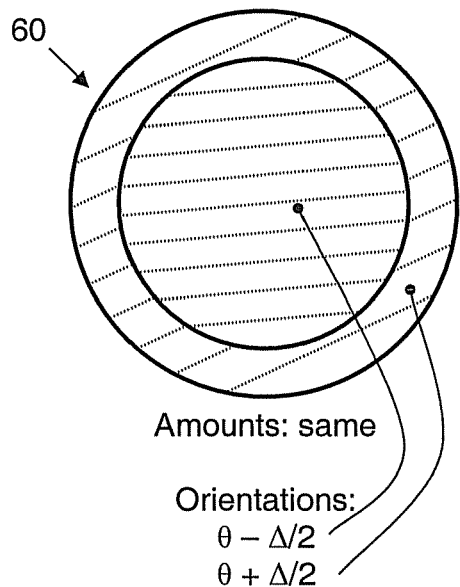
FIG. 6 is a schematic drawing of a pupil of an intraocular lens with two concentric zones, in which the central zone has a radius different than half the radius of the full pupil.

In the pupil 60 of FIG. 6, the central zone may have a radius greater than half the radius of the full pupil. The astigmatism amounts are the same in each zone, and the astigmatism orientations are angularly separated by $\Delta$. Although not shown in the figures, the central zone may also have a radius less than half the radius of the full pupil.

Figure 7:
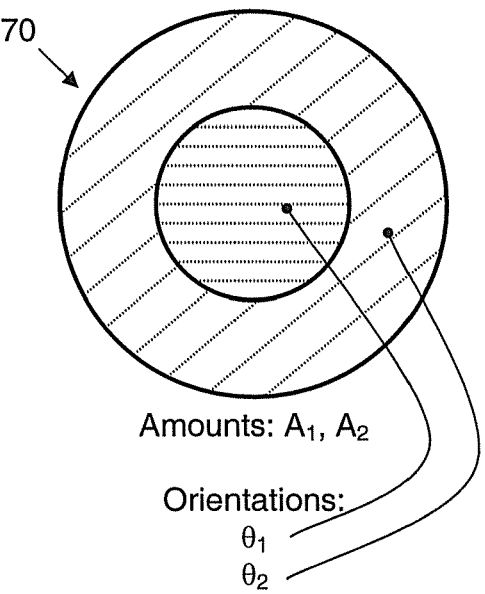
FIG. 7 is a schematic drawing of a pupil of an intraocular lens with two concentric zones, in which each zone has both s different astigmatism amount and a different astigmatism orientation.

In the pupil 70 of FIG. 7, the astigmatism amounts may be different in the central and outer zones.

Figure 8:
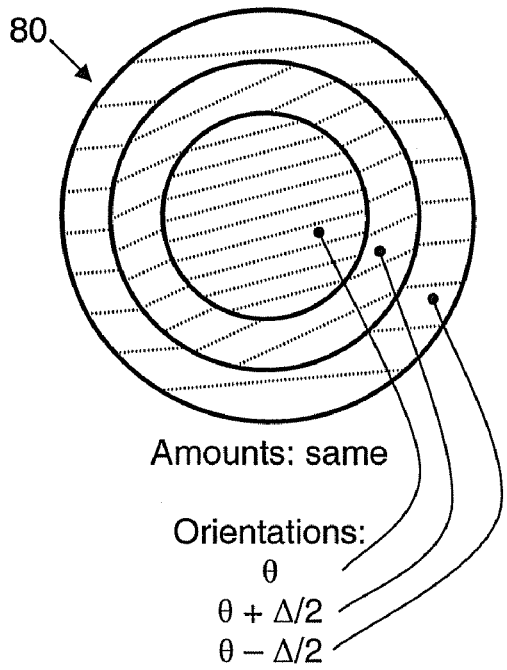
FIG. 8 is a schematic drawing of a pupil of an intraocular lens with three concentric zones.

In the pupil 80 of FIG. 8, there are three concentric zones, rather than two as in FIGS. 4, 6 and 7. The astigmatism amounts may be the same in all three zones. Alternatively, the astigmatism amounts may be the different in one or more zones, or different in all the zones. The astigmatism orientations may be different in all three zones, for example, with the orientation in one zone falling halfway between the orientations in the remaining two zones. In some embodiments, the orientation of the zones may be selected depending on the amount of astigmatism in each zone.

Figure 9:
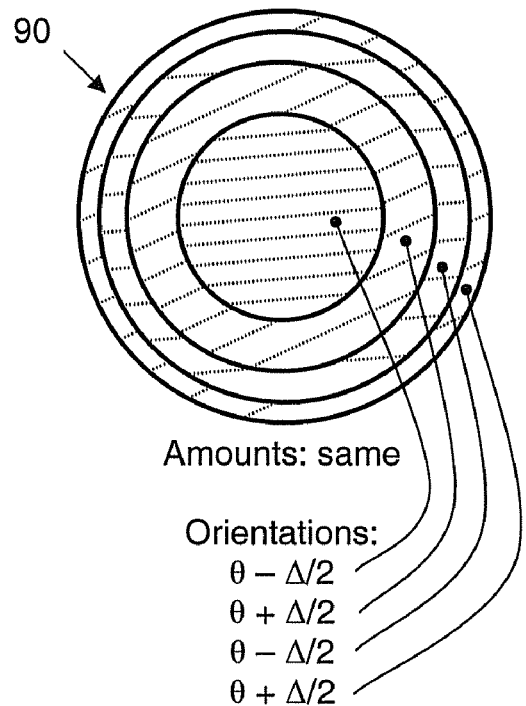
FIG. 9 is a schematic drawing of a pupil of an intraocular lens with four concentric zones, in which each zone has the same astigmatism amount and a different astigmatism orientation.

In the pupil 90 of FIG. 9, there are four concentric zones. The astigmatism amounts are the same in all four zones. The astigmatism orientations alternate between $\theta+\Delta/2$ and $\theta-\Delta/2$, when aligned to a cornea having an astigmatism orientation of $\theta$.

Figure 10:
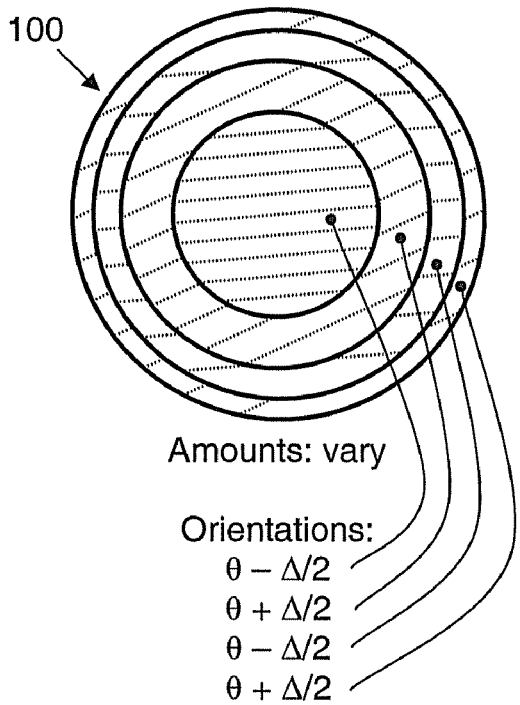
FIG. 10 is a schematic drawing of a pupil of an intraocular lens with four concentric zones, in which each zone has both a different astigmatism amount and a different astigmatism orientation.

In the pupil 100 of FIG. 10, the astigmatism amounts vary from zone-to-zone. The four zones may all have different astigmatism amounts, or at least one zone may have the same astigmatism amount as another zone.

Figure 11:
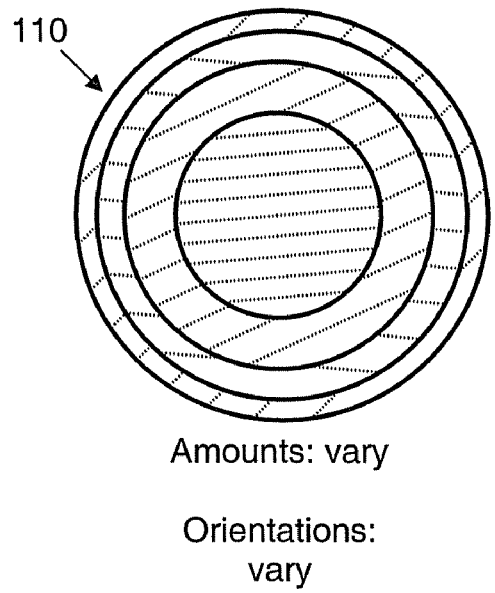
FIG. 11 is a schematic drawing of a pupil of an intraocular lens with four concentric zones, in which each zone has both a different astigmatism amount and a different astigmatism orientation.

In the pupil 110 of FIG. 11, both the astigmatism amounts and the astigmatism orientations may vary from zone-to-zone. The four zones may all have different astigmatism orientations, or at least one zone may have the same astigmatism orientation as another zone.

As a further alternative not shown in the figures, there may be additional concentric zones, numbering five, six, or any suitable value more than six. The astigmatism amounts and/or orientations may be the same in all the zones, may be different in at least two zones, or may be different in all the zones.

In addition to having purely concentric zones, the lens pupil may optionally have one or more of the concentric zones further divided into one or more azimuthal zones. For instance, the pupil 120 in FIG. 12 has a central zone, surrounded on one side by one azimuthal zone and on the opposite side by a second azimuthal zone. The zones may all have the same astigmatism amounts. The two azimuthal zones in pupil 120 have astigmatism orientations that differ from each other by angle $\Delta$ and differ from the central zone by $\Delta/2$. Alternatively, the astigmatism orientations of the azimuthal zones may have any particular orientation with respect to the central zone and to each other. Note that in FIG. 12 the boundary between the azimuthal zones is aligned with the astigmatism orientation in the central zone. Alternatively, this boundary may be at an angle to the astigmatism orientation in the central zone.

Figure 12:
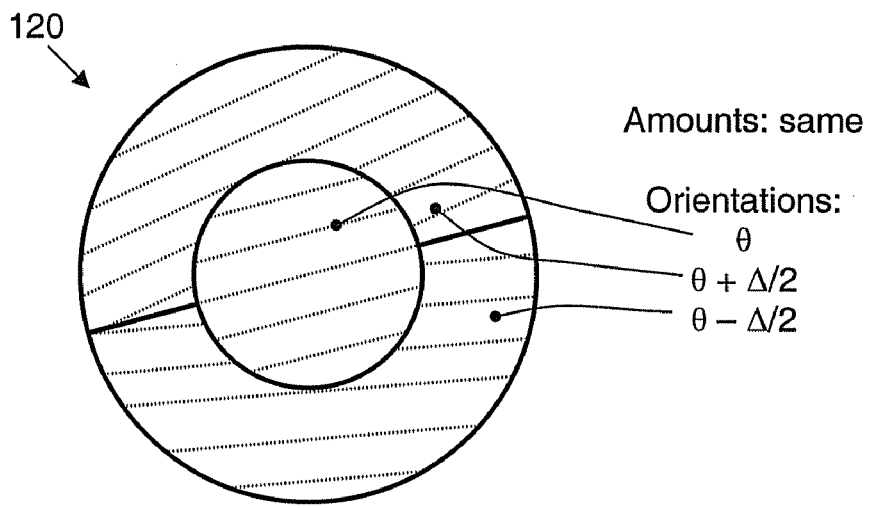
FIG. 12 is a schematic drawing of a pupil of an intraocular lens with two azimuthal zones.
Figure 13:
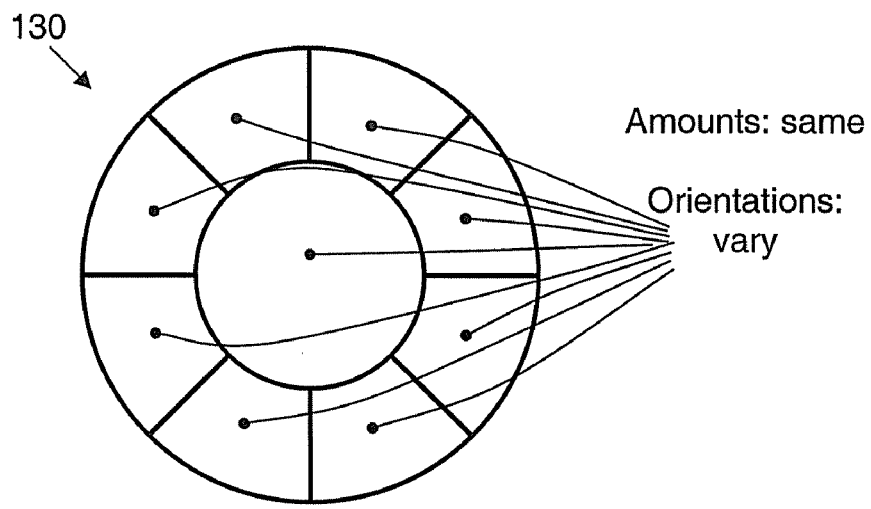
FIG. 13 is a schematic drawing of a pupil of an intraocular lens with eight azimuthal zones, in which each zone has the same astigmatism amount and a different astigmatism orientation.

In the pupil 130 of FIG. 13, there are eight azimuthal zones, rather than the two shown in pupil 120 of FIG. 12. The astigmatism amounts are the same in all the zones, and the astigmatism orientations may be different in one or more zones. Note that the azimuthal zones of pupil 130 all subtend the same azimuthal angle. Alternatively, one or more azimuthal zones may subtend a different azimuthal angle from any another azimuthal zone. Alternatively, there may be more or fewer than eight azimuthal zones.

Figure 14:
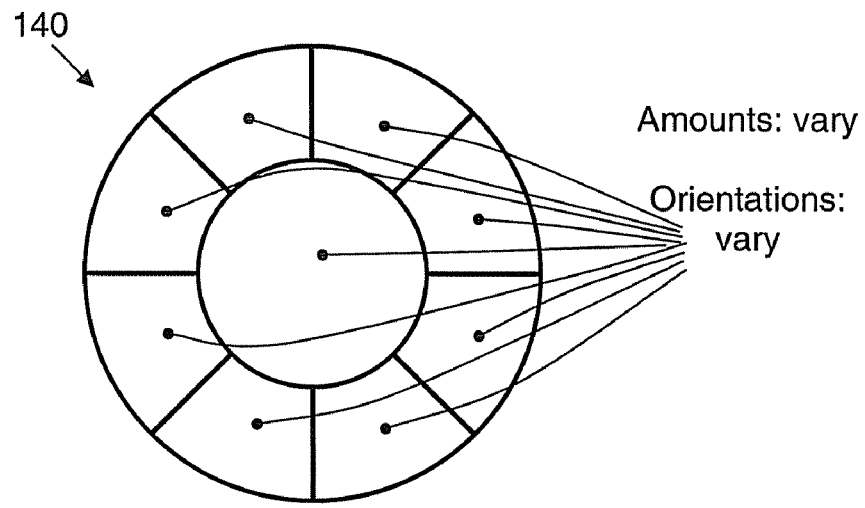
FIG. 14 is a schematic drawing of a pupil of an intraocular lens with eight azimuthal zones, in which each zone has both a different astigmatism amount and a different astigmatism orientation.

In the pupil 140 of FIG. 14, both the astigmatism amounts and the astigmatism orientations may differ from zone-to-zone.

Although the lenses in FIGS. 4 and 6-14 have circular, concentric zones, other zone shapes may be used as well. For instance, a particular zone may be elliptical, or elongated in a particular dimension. Or, a particular zone may be spiral-shaped, have a straight or curved edge, have one or more corners, or may be any other suitable shape.

The lens pupils shown schematically herein show only the spatial locations (x, y) of lens astigmatism amounts and orientations. The source of this lens astigmatism may be any combination of a toric or anamorphic anterior refractive surface, a toric or anamorphic posterior refractive surface, and a diffractive element made integral with or attached to the anterior surface and/or the posterior surface. The toric or anamorphic surfaces may have a cross-section that may be spherical in shape, or may optionally have aspheric terms and/or a non-zero conic constant.

In some embodiments, a lens comprises more zones than those illustrated in FIGS. 4-14. In other embodiments, portions of the lens or the entire lens may be configured so that the amount of astigmatism or the orientation of an astigmatism varies continuously between adjacent zone.

For purposes of illustration, embodiments of the present invention have been directed to intraocular lenses; however, other types of lenses and ophthalmic lenses are anticipated. For example, embodiments of the present invention may be incorporated into contact lenses, corneal inlays, spectacles, or any suitable ophthalmic lens. In addition, embodiments of the present invention may be incorporated various types of ophthalmic lenses, for example, single-focus (monofocal) lenses, refractive lenses, diffractive lenses, dual-focus or bifocal lenses (refractive and/or diffractive), multifocal lenses (refractive and/or diffractive), or accommodating lenses move or change shape in order to provide varying amounts of diopter power.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A multi-zonal ophthalmic lens comprising:
   an optic having a pupil;
   a first zone having a first astigmatism, the first astigmatism having a first astigmatism magnitude and a first astigmatism orientation; and
   a second zone surrounding the first zone and having a second astigmatism, the second astigmatism having a second astigmatism magnitude equal to the first astigmatism magnitude and a second astigmatism orientation different from the first astigmatism orientation,
   an average axis of orientation of astigmatism of all zones of the ophthalmic lens, the average axis configured to be aligned to an astigmatic axis of an eye, the astigmatic axis of the eye having a constant magnitude and orientation;
   wherein, when the ophthalmic lens disposed within the eye, the ophthalmic lens is less sensitive to rotational misalignment between the average axis and the astigmatic axis of the eye than a reference optic having first and second zones that are equal to the first and second zones of the ophthalmic lens, except that the first and second zones of the reference optic have a same astigmatism orientation.

2. The multi-zonal ophthalmic lens of claim 1, wherein the first and second zones are circular and concentric.

3. The multi-zonal ophthalmic lens of claim 1, wherein the first zone includes the center of the pupil and the second zone extends from the first zone to the edge of the pupil.

4. The multi-zonal ophthalmic lens of claim 1, further comprising a third zone surrounding the second zone and having a third astigmatism, the third astigmatism having a third astigmatism magnitude and a third astigmatism orientation, wherein, when the ophthalmic lens disposed within the eye, the ophthalmic lens is less sensitive to rotational misalignment between the average axis and the astigmatic axis of the eye than the reference optic, the reference optic comprising a third zone equal to the third zone of the ophthalmic lens, except that the third zone of the reference optic has a same astigmatism orientation as the first and second zones of the reference optic.

5. The multi-zonal ophthalmic lens of claim 4,
   wherein the first, second and third astigmatism magnitudes are all equal; and
   wherein the first and third astigmatism orientations are equal and are different from the second astigmatism orientation.

6. The multi-zonal ophthalmic lens of claim 4,
   wherein the first, second and third astigmatism magnitudes are all equal; and
   wherein the first, second and third astigmatism orientations are all different.

7. The multi-zonal ophthalmic lens of claim 4, further comprising a fourth zone surrounding the third zone and having a fourth astigmatism, the astigmatism having a fourth astigmatism magnitude and a fourth astigmatism orientation, wherein, when the ophthalmic lens disposed within the eye, the ophthalmic lens is less sensitive to rotational misalignment between the average axis and the astigmatic axis of the eye than the reference optic, the reference optic comprising third and fourth zones equal to the third and fourth zones of the ophthalmic lens, except that the third and fourth zones of the reference optic have a same astigmatism orientation as the first and second zones of the reference optic.

8. The multi-zonal ophthalmic lens of claim 7,
   wherein the first, second, third and fourth astigmatism magnitudes are all equal; and
   wherein the first and third astigmatism orientations are equal; and
   wherein the second and fourth astigmatism orientations are equal and are different from the first and third astigmatism orientations.

9. The multi-zonal ophthalmic lens of claim 7,
   wherein the first, second, third and fourth astigmatism magnitudes are all equal; and
   wherein the first, second, third and fourth astigmatism orientations are all different.

10. The multi-zonal ophthalmic lens of claim 1, wherein the second zone comprises a first azimuthal zone and a second azimuthal zone, the first and second azimuthal zones having astigmatisms with magnitudes equal to each other and equal to the first astigmatism magnitude and orientations different from each other and different from the first astigmatism orientation.

11. The multi-zonal ophthalmic lens of claim 1, wherein the astigmatism orientation of the first and second zones are independent of an astigmatic condition of the eye.

12. The multi-zonal ophthalmic lens of claim 1, wherein the average axis bisects the first astigmatism orientation and the second astigmatism orientation.

* * * * *